US010537648B2

(12) United States Patent
Ghosh et al.

(10) Patent No.: US 10,537,648 B2
(45) Date of Patent: Jan. 21, 2020

(54) COMPOSITIONS AND METHODS FOR VISUALIZATION OF THE VITREOUS

(71) Applicant: NOVARTIS AG, Basel (CH)

(72) Inventors: Joy Ghosh, Boston, MA (US); Thaddeus Peter Dryja, Milton, MA (US); Michael Roguska, Ashland, MA (US); Eric C. Carlson, Burleson, TX (US)

(73) Assignee: Novartis AG, Basel (CH)

( * ) Notice: Subject to any disclaimer, the term of this patent is extended or adjusted under 35 U.S.C. 154(b) by 64 days.

(21) Appl. No.: 15/321,025

(22) PCT Filed: Jun. 24, 2015

(86) PCT No.: PCT/IB2015/054747
§ 371 (c)(1),
(2) Date: Dec. 21, 2016

(87) PCT Pub. No.: WO2015/198245
PCT Pub. Date: Dec. 30, 2015

(65) Prior Publication Data
US 2017/0202981 A1 Jul. 20, 2017

Related U.S. Application Data

(60) Provisional application No. 62/016,731, filed on Jun. 25, 2014.

(51) Int. Cl.
*A61K 51/08* (2006.01)
*A61K 49/00* (2006.01)
*A61K 9/00* (2006.01)

(52) U.S. Cl.
CPC ........ *A61K 49/0056* (2013.01); *A61K 9/0051* (2013.01)

(58) Field of Classification Search
CPC ...... A61K 49/00; A61K 49/0056; A61K 9/00; A61K 9/0051; A61K 2123/00; A61K 2121/00; A61K 31/728; A61K 38/00; A61K 38/02; A61K 49/001; A61K 49/0013; A61K 49/0015; A61K 49/0017; A61K 49/0019; A61K 49/0036; A61K 49/0041; A61K 49/0043; A61K 49/0047; A61K 49/005; A61K 49/06; A61K 49/14; A61K 51/00; A61K 51/08
USPC .......... 424/1.11, 1.49, 1.65, 1.69, 1.73, 1.81, 424/1.85, 1.89, 9.1, 9.2, 9.3, 9.4, 9.5, 9.6; 514/1, 1.1; 534/7, 10–16; 530/30
See application file for complete search history.

(56) References Cited

U.S. PATENT DOCUMENTS 8,580,735 B2 * 11/2013 Francois ................ A61K 38/12
514/12.2
2013/0143814 A1 6/2013 Rosa et al.
2014/0186350 A1 7/2014 Ghosh et al.

FOREIGN PATENT DOCUMENTS

| WO | 2006/133903 | 12/2006 |
| WO | 2010/074325 | 7/2010 |
| WO | WO 2012/135432 | 10/2012 |
| WO | 2013/063155 | 5/2013 |
| WO | 2014/011813 | 1/2014 |
| WO | 2014/099997 | 6/2014 |

OTHER PUBLICATIONS

Basabe-Desmonts et al., "Design of Fluorescent Materials for Chemical Sensing" Chemical Society Reviews 36:993-1017, 2007.
Day et al.,"Hyaluronan-binding Proteins: Tying up the Giant" J. Bio. Chem. 277(7):4585-4588, 2002.
Fraser et al., "Plasma Clearance, Tissue Distribution and Metabolism of Hyaluronic Acid Injected Intravenously in the Rabbit" Biochem. J. 200(2):415-424, 1981.

(Continued)

*Primary Examiner* — D. L. Jones
(74) *Attorney, Agent, or Firm* — Patrick M. Ryan

(57) ABSTRACT

The invention provides compositions for rendering a vitreous cavity visible during a surgical procedure to alleviate a structural disorder caused by the vitreous in an eye, and methods of using the compositions. The compositions are vitreous delineating agents that comprise a hyaluronan binding peptide linked to an optically detectable moiety. Such compositions can be in a formulation that may be a solution, a suspension, or an emulsion, and would be injected into the vitreous shortly prior to use. The composition may additionally contain a therapeutic agent, a diagnostic agent, or a chemosensing material, in use, the composition marks or delineates the vitreous by binding preferentially to the hyaluronan that permeates the vitreous humor and binding little or not at all to surrounding tissues such as the retina. The interface between the labelled vitreous humor and the non-labelled surrounding vital tissues produces a visible signal, thereby allowing a surgeon to clearly visualize the entire vitreous cavity and distinguish it from vital ocular structures. Use of the method improves the accuracy and safety of a vitrectomy and thus prevents suboptimal outcomes or the need for repeated procedures. The compositions comprising chemosensing material are useful as long-lasting biosensors, which when used in the vitreous enable repetitive, non-invasive, in vivo measurements of metabolites or pharmacologic agents in the vitreous of animals or humans.

4 Claims, 7 Drawing Sheets
Specification includes a Sequence Listing.

(56) References Cited

OTHER PUBLICATIONS

Gentz et al., "Bioassay for Trans-Activation Using Purified Human Immunodeficiency Virus Tat-Encoded Protein: Trans-Activation Requires mRNA Synthesis" Proc. Natl. Acad. Sci. USA 86(3):821-824, 1989.
Griss et al., "Bioluminescent Sensor Proteins for Point-of-Care Therapeutic Drug Monitoring" Nature Chemical Biology 10:598-603, 2014.
Knittel et al., "Comparison of Oxycodone in Vitreous Humor and Blood Using EMIT® Screening and Gas Chromatographic—Mass Spectrometric Quantitation" J. Anal. Toxicol. 33:433-438, 2009.
Laurent and Fraser, "Turnover of Hyaluronate in the Aqueous Humour and Vitreous Body of the Rabbit" Experimental Eye Research 36(4):493-503, 1983.
Laurent and Fraser, "The Properties and Turnover of Hyaluronan" Ciba Foundation 124:9-29, 1986.
Mahoney et al., "Mapping the Hyaluronan-binding Site on the Link Module from Human Tumor Necrosis Factor-stimulated Gene-6 by Site-directed Mutagenesis" J. Bio. Chem 276:25, 22764-22771, 2001.
Mao et al., "Sortase-Mediated Protein Ligation: a New Method for Protein Engineering" J Am Chem Soc. 126(9):2670-2671, 2004.
Necas, "Hyaluronic Acid (Hyaluronan): a Review" Veterinarni Medicina 53(8):397-411, 2008.
Wilson et al., "The Structure of an Antigenic Determinant in a Protein" Cell 37:767-768, 1984.
Yang, et al., "Identification of a Common Hyaluronan Binding Motif in the Hyaluronan Binding Proteins RHAMM, CD4 and Link Protein" EMBO Journal 13(2):286-296, 1994.

\* cited by examiner

COMPOSITIONS AND METHODS FOR VISUALIZATION OF THE VITREOUS

CROSS-REFERENCE TO RELATED APPLICATIONS

This is application is a 371 National Stage Application of International Application No. PCT/IB2015/054747, filed Jun. 24, 2015, which claims benefit of U.S. Provisional Application No. 62/016,731, filed Jun. 25, 2014, each of which in its entirety are herein incorporated by reference.

FIELD OF THE INVENTION

The invention relates to compositions, methods, and uses for protein-based, long-lasting agents for injection into the vitreous humor in mammalian eyes. The invention also relates to the use of such compositions during ophthalmic surgery, for example, during vitrectomy surgery, and their use as biosensors.

BACKGROUND OF THE INVENTION

In the eye, the cavity between the lens and the retina is filled with a clear, jelly-like substance termed the vitreous body, vitreous humor, or vitreous. Its volume is fixed and is relatively permanent. The vitreous humor is 99% water, with most of the remaining 1% composed of salts (sodium, chloride, bicarbonate, etc.), collagen, and hyaluronan (hyaluronic acid). The collagen and hyaluronan give the vitreous is gel-like consistency and high viscosity. The outer surface of the vitreous is normally weakly adherent to the retina and ciliary body, with a somewhat tighter attachment at the macula, at the far periphery of the retina near the ora serrata, and at the pars plana of the ciliary body. In pathological conditions such as rhegmatogenous retinal detachment, macular hole, vitreomacular traction syndrome, and proliferative vitreoretinopathy, the attachment of the vitreous to the retina mediates or facilitates damage to the retina. For example, as the vitreous ages, its collagen contracts (a process called vitreous syneresis), and the contraction can produce traction on the retina ultimately inducing a tear or hole in the retina and a consequent retinal detachment or macular hole. As another example, the attachment may serve as a scaffold for fibrous, fibrovascular, or fibroglial proliferation emanating from the retina, a process called proliferative vitreoretinopathy. The fibrous membranes in proliferative vitreoretinopathy can contract and cause retinal tears, retinal holes, and retinal detachments, all of which can lead to blindness.

A patient suffering from these and some other vitreous-mediated diseases may benefit from a surgical procedure known as a vitrectomy. Vitrectomy can also be step in the process of other types of retinal surgery. Examples include the vitrectomy that typically accompanies the removal of foreign bodies that may have entered the vitreous body traumatically or iatrogenically, or the vitrectomy that accompanies the injection of a gene therapy vector under the retina, or the vitrectomy performed in eyes with infectious endophthalmitis to remove microorganisms and make space for the injection of antibiotics. However, the surgical procedure of vitrectomy itself can produce complications.

Many surgical procedures of the retina, such as the removal of epiretinal membranes, require complete dissection of the vitreous away from the retina to be optimally efficacious. The transparency of vitreous makes it challenging for the surgeon to visualize and hence completely remove the vitreous. A surgeon performing a vitrectomy may not be absolutely certain whether the posterior surface of the vitreous (called the posterior hyaloid) is completely separated from the retina and whether a complete vitrectomy has been achieved. While the surgeon attempts a complete removal of the vitreous near the retina, he or she may inadvertently cut into the retina and thereby create iatrogenic retinal defects or holes or possibly remove irreplaceable neural elements essential for vision. Many surgical techniques have been described which attempt to aid the surgeon in the removal of the posterior hyaloid during vitrectomy. These include the use of various cannulas, forceps, or vitreous-cutting devices with active or passive suction applied to engage and separate the posterior hyaloid from the retina. Ryan et al. have described the use of injected autologous blood for improved visualization of cortical vitreous during posterior hyaloid separation. None of these is completely satisfactory. For example, the instillation of blood into the vitreous has several drawbacks: blood disperses into the vitreous cavity and is likely to obscure visualization of the retina during vitrectomy, and it has the potential of causing postoperative inflammation and proliferative vitreoretinopathy.

In summary, iatrogenic damage to the retina is still a recognized potential complication of vitrectomy. A need still exists for a method to surgically remove the vitreous with improved accuracy, precision, and completeness so that complications, as well as discomfort, inconvenience, and expense to the patient, may be minimized. Thus, methods and agents to improve the visualization of the vitreous during a surgical procedure, and hence to ensure the accuracy of the procedure, are desirable to achieve better functional and anatomical outcomes.

SUMMARY OF THE INVENTION

The invention is directed to a method to alleviate a structural disorder of an eye. In certain aspects, the method comprises injecting a vitreous-delineating composition into the eye in an effective amount to allow the vitreous to be visible to a surgeon while simultaneously maintaining the view of intraocular structures such as the retina, thereby enabling the surgeon to alleviate the disorder in a safer and more efficacious manner.

The composition may comprise a therapeutic agent, an inert agent, or an inert agent that contains a therapeutic agent, such as a microsphere or liposome containing a therapeutic agent.

The composition may be in a formulation such as a solution, an emulsion, or a suspension.

The invention is additionally directed to a composition for visualizing a vitreous cavity in a mammalian eye during surgery. The composition is a vitreous delineating agent that binds hyaluronan throughout the vitreous humor to render the vitreous gel visible to the surgeon. The formulation of the composition is preferably injectable, and may be translucent, fluorescent, phosphorescent, opaque, or semi-opaque.

The invention provides a surgical method to alleviate a disorder of an eye caused or mediated by the vitreous comprising: injecting into the eye a composition comprising a peptide that binds hyaluronan (HA) which is linked to an optically detectable moiety. The dose injected into the eye would provide an amount effective to render the vitreous visible for surgically correcting the disorder by removing the vitreous.

The invention further provides a composition for visualizing the vitreous in a mammalian eye comprising an injectable formulation of a peptide that binds hyaluronan (HA) linked to an optically detectable moiety as a vitreous delineating agent in an effective amount that associates with HA in the vitreous to render it visible to a surgeon.

The invention further provides an ophthalmic composition for visualizing the vitreous in a mammalian eye comprising a peptide that binds hyaluronan (HA) linked to an optically detectable moiety in an effective amount that associates with HA in the vitreous to render the vitreous visible when a signal is generated by the detectable moiety.

The invention also provides a method of staining the vitreous in a mammalian eye comprising (a) injecting a composition comprising a peptide that binds hyaluronan (HA) linked to an optically detectable moiety into the mammalian eye and (b) applying an energy source (e.g., a light or laser light) to the eye to generate a signal from the detectable moiety.

In certain aspects, the optically detectable moiety is luminescent, photoluminescent, electroluminescent, bioluminescent, chemiluminescent, fluorescent, or phosphorescent, or is a chromophore.

In other aspects, the peptide comprises a sequence selected from the group consisting of:

a) SEQ ID NO: 2, SEQ ID NO: 3, SEQ ID NO: 4, SEQ ID NO: 5, SEQ ID NO: 6, SEQ ID NO: 7, SEQ ID NO: 8 and SEQ ID NO: 9, SEQ ID NO: 10, SEQ ID NO: 11, SEQ ID NO: 12 and SEQ ID NO: 13; or b) 95 consecutive amino acids of the sequence of SEQ ID NO: 2, SEQ ID NO: 3, SEQ ID NO: 4, SEQ ID NO: 5, SEQ ID NO: 6, SEQ ID NO: 7, SEQ ID NO: 8 and SEQ ID NO: 9, SEQ ID NO: 10, SEQ ID NO: 11, SEQ ID NO: 12 and SEQ ID NO: 13.

In other aspects, a composition of the invention further includes a therapeutic agent that is, for example, an anti-infective agent, an immunosuppressant agent, an anti-proliferative agent, an anti-angiogenesis agent, a wound healing agent, an anti-scarring agent, or combinations thereof.

In one aspect, a composition of the invention is injected prior to or during a vitrectomy.

Another aspect of the invention includes peptide tagged molecules linked to optically detectable moieties. In certain aspects of the invention, the compositions may comprise a peptide that binds, or is capable of binding, hyaluronan (HA). In certain aspects the HA peptide composition binds HA in the eye with a KD of less than or equal to 100 µM, 90 µM, 80 µM, 70 µM, 60 µM, 50 µM, 40 µM, 30 µM, 20 µM, or 10 µM. In certain preferred embodiments, a composition of the invention binds HA in the eye with a KD of less than or equal to 9.0 µM. For example, the peptide can bind HA with a KD of less than or equal to, 8.5 µM, 8.0 µM, 7.5 µM, 7.0 µM, 6.5 µM, 6.0 µM, 5.5 µM, 5.0 µM, 4.5 µM, 4.0 µM, 3.5 µM, 3.0 µM, 2.5 µM, 2.0 µM, 1.5 µM, 1.0 µM or 0.5 µM. In one aspect the peptide binds HA with a KD of less than or equal to 8.0 µM. In one aspect the peptide binds HA with a KD of less than or equal to 7.2 µM. In one aspect the peptide binds HA with a KD of less than or equal to 5.5 µM. In certain specific aspects, the peptide may comprise a sequence of SEQ ID NO: 1, 2, 3, 4, 5, 6, 7, 8, 9, 10, 11, 12, or 13. It is also contemplated that the peptide tag is linked to a therapeutic agent, such as a protein or a nucleic acid.

These and other aspects of the invention will be apparent in light of the following figures and detailed description.

DETAILED DESCRIPTION

Figure 1:
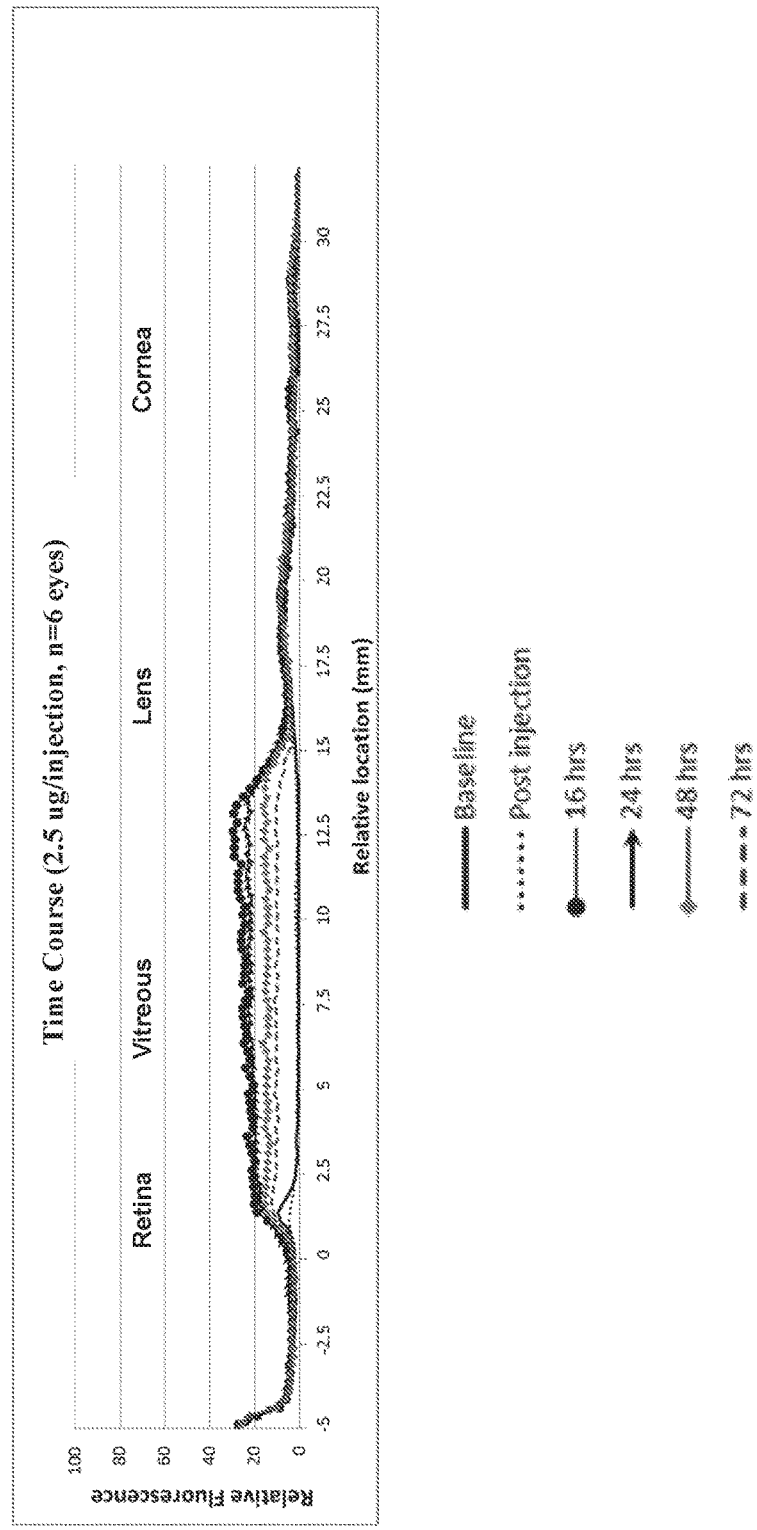
FIG. 1 shows time related relative fluorescence change, especially in the vitreous body of rabbit eyes after IVT administration of a composition of the invention at 2.5 µg (mean value, n=6 eyes).

Compositions comprising a peptide that binds hyaluronan (HA) linked to an optically detectable moiety are provided. As described herein, in certain embodiments a composition of the invention can be used, for example, as a vitreous delineating composition (for example to facilitate ocular surgery), as a sensor composition (for example to monitor and assess the presence of a desired analyte in the vitreous), and as a intravitreal pH assessing composition.

The use of one or more vitreous delineating compositions comprising a peptide that binds hyaluronan (HA) linked to an optically detectable moiety to improve visualization of the vitreous during surgery to alleviate a structural disorder of an eye is disclosed. Delineation of the vitreous assists the surgeon in separation of the posterior hyaloid and complete removal of vitreous during a procedure such as a pars plana vitrectomy. The composition is introduced into the vitreous and binds to hyaluronan in the eye throughout the vitreous humor, increasing the visualization of the vitreous throughout. The visible vitreous delineating agent, provided for example as a solution, suspension or emulsion, diffuses throughout the vitreous over the course of a few hours. In doing so, the vitreous is now in sharp contrast with the fundus and allows the surgeon to clearly distinguish the vitreous from the retina. The localization of the composition to the vitreous and not the retina is due to the composition's affinity for hyaluronan and the much higher concentration of hyaluronan in the vitreous compared to the retina or to any other ocular structures. In fact, the hyaluronic acid concentration in the vitreous (0.1 to 0.4 mg/ml) is higher than almost any other tissue of the human body. The delineating composition is preferably an inert agent, lacking pharmacologic activity thereby making it safe and not associated with toxicity or adverse reactions prior to or during a surgery. The composition is preferably delivered into an eye by injection. It diffuses through the vitreous and forms reversible complexes with hyaluronan in the vitreous. Because the composition can be colored or otherwise optically apparent (e.g., innately or detectable upon contact with an energy source), it delineates or demarcates the vitreous and in effect "lights up" the vitreous humor by a visible signal generated by the optically detectable moiety under the appropriate conditions. This improves visualization of the vitreous and its posterior hyaloid for the surgeon. In certain embodiments, a vitreous delineating composition of the invention can be visualized episodically or transiently at any time during surgery and at the will of the surgeon by the surgeon or surgical assistant applying an energy source such that the composition exhibits fluorescent properties. In certain embodiments, a vitreous delineating composition of the invention can be visualized continually, for example during the course of a surgery.

In certain embodiments, a composition of the invention can be rendered visible to the surgeon during surgery. For example, the composition is injected before or during a surgery, and an energy source (such as a light) can be used to excite an optically detectable moiety of a composition of the invention thereby causing the moiety to exhibit fluorescent properties. Visualization may be with the naked eye or with the assistance of instrumentation such as an operating microscope depending on the moiety used in a composition of the invention.

One of skill in the art can readily determine a suitable detectable substance as an optically detectable moiety based on the intended use of a composition of the invention. For instance, in a surgical method of the invention, a composition comprising a fluorescent moiety may be preferred, thus enabling a surgeon to view the vitreous at will by turning on a light energy source with a particular wavelength and intensity to excite the substance for visualizing the vitreous at any time during a surgery, and turning off the light energy source so the composition is not visible when necessary during the surgical procedure. If a surgeon removed vitreous as part of the procedure (i.e., during a vitrectomy), the agent would disappear along with the vitreous. Regions of vitreous cavity with residual vitreous could be easily recognized and the surgeon could devote attention to those areas. Complete absence of the color or fluorescence in the vitreous would indicate that the vitrectomy was complete.

Vitreous concentrations of drugs correlate with their concentrations in blood, with the correlations dependent on physicochemical properties of the drugs (e.g., their solubility and lipophilicity). Forensic specialists sometimes measure the levels of drugs or toxins in the vitreous as a surrogate to measuring them in the blood (for example, see Knittel et al., 2009, *J. Anal. Toxicol.* 33:434-438). Accordingly, a sensor composition of the invention as described herein can be used to measure metabolic and pharmacologic changes in the eye and in the body once residing in the vitreous. A composition of the invention can be used to assess and monitor in vivo drugs and/or metabolites in the vitreous, thus providing long-lasting "biosensors" in the vitreous that provide a visual signal correlating with a chemical compound of interest. Compositions of the invention can be used, for example, to allow in vivo, repeated measurements in animals thereby reducing the numbers of animals typically used for such studies and improving the accuracy of the measurements, since each eye can be followed longitudinally over time.

Compositions

In certain embodiments, the invention provides a composition comprising a peptide that binds hyaluronan (HA) linked to an optically detectable moiety.

A composition of the invention can further comprise a therapeutic agent and/or an inert substance in addition to an HA-binding peptide with or without an optically detectable moiety.

As used herein, the term "therapeutic agent" refers to a compound, such as a protein, nucleic acid or small molecule, useful to treat, prevent or ameliorate a disease, condition or disorder. Non-limiting examples of a therapeutic agent useful in a composition of the invention include an anti-infective agent, an immunosuppressant agent, an anti-proliferative agent, an anti-angiogenesis agent, a wound healing agent, and an anti-scarring agent. Combinations thereof can also be included in a composition of the invention.

As used herein, the term "inert substance" refers to a substance that is chemically and pharmacologically inactive in the eye, including but not limited to a blank microsphere or liposome. An inert substance useful in a composition of the invention is a substance that is visible or can be rendered visible during the surgical procedure. A combination of therapeutic agents and inert substances can be used (for example, a microsphere or liposome containing any of the above therapeutic agents).

A composition of the invention can further comprise a diagnostic agent. The diagnostic agent can be used to detect, assess, and/or monitor progression of a disorder or disease of the eye.

Optically Detectable Moieties

As used herein, an "optically detectable moiety" is any substance that can be detected when exposed to certain conditions, and can be a contrasting agent. In certain embodiments, the optically detectable moiety is luminescent, photoluminescent, electroluminescent, bioluminescent, chemiluminescent, fluorescent, or phosphorescent, or is a chromophore. For example, a fluorescent moiety can be excited by exposure to an energy source (e.g., a light) having a specific wavelength and intensity, thereby enabling the composition of the invention to be seen, for example using a surgical microscope with particular filters as known in the art. A contrasting agent is a substance that is opaque, for example, to visible light, or is otherwise visibly distinguishable from the vitreous under certain conditions (e.g., in visible light).

Detectable substances suitable for use in a composition of the invention include, but are not limited to, various enzymes, such as, but not limited to, horseradish peroxidase, alkaline phosphatase, beta-galactosidase, or acetylcholinesterase; prosthetic groups, such as, but not limited to, streptavidinlbiotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminal; bioluminescent materials, such as but not limited to, luciferase, luciferin, and aequorin; radioactive materials, such as, but not limited to, iodine ($131I$, $125I$, $123I$, and $121I$,), carbon ($14C$), sulfur ($35S$), tritium ($3H$), indium ($115In$, $113In$, $112In$, and $111In$,), technetium ($99Tc$), thallium ($201Ti$), gallium ($68Ga$, $67Ga$), palladium ($103Pd$), molybdenum ($99Mo$), xenon (133Xe), fluorine (18F), 153Sm, 177Lu, 159Gd, 149Pm, 140La, 175Yb, 166Ho, 90Y, 47Sc, 186Re, 188Re, 142Pr, 105Rh, 97Ru, 68Ge, 57Co, 65Zn, 85Sr, 32P, 153Gd, 169Yb, 51Cr, 54Mn, 75Se, 113Sn, and 117Tin; phosphorescent materials, such as but not limited to those including pigments like zinc sulfide or strontium aluminate; halochromic molecules that change color based on pH, such as but not limited to phenolphthalein; and positron emitting metals using various positron emission tomographies, and non-radioactive paramagnetic metal ions.

Further, a colored substance can be used in a composition of the invention as the optically detectable moiety. As used herein, a "colored substance" preferably has no bioactivity, and is present in a sufficiently low dose so as to maintain visualization of the fundus when injected into the eye. Examples of colored substances that can be used in a composition of the invention include polylactic acid particles and polylactic acid.

In certain embodiments, an HA-binding peptide is linked to an halochromic molecule, and is useful for determining the pH in a mammalian eye non-invasively and in vivo. Halochromic molecules change color according to the pH of their environment. In a preferred embodiment, the halochromic molecule can change color, and is therefore detectable, in the physiologic pH range of around 7.0 to 7.6. A single intravitreal injection of a composition of the invention can be used to repeatedly measure intraocular pH over the course of hours, days, and weeks by checking the color of the vitreous at desired time points.

In certain other embodiments, an HA-binding peptide is linked to a fluorescent chemosensing material. Such sensor compositions are useful for monitoring the presence of a desired chemical species as described, for example, in Basabe-Desmonts et al., 2007, *Chemical Society Reviews* 36:993-1017, the contents of which are incorporated by reference in its entirety.

Suitable chemosensing materials include, but are not limited to, fluorescent polymers, sol-gel materials, mesoporous materials, surfactant aggregates, silica and polymer-based nanoparticles, and quantum dots.

A sensor composition of the invention can be designed to measure any desired compound, such as therapeutic drug and physiologic metabolites. Such sensors can be useful for monitoring and assessing the presence of certain molecules for days, weeks, and months after injection into the eye or after entering the eye from the blood or from pericoular tissues such as the conjunctiva or orbital tissues, provided that the sensor is linked to a peptide like HA10 that mediates a long residence time in the vitreous, as described herein. Standard optical techniques, such as but not limited to a fluorophotometer instrument, can be used to monitor fluorescence of a sensor composition of the invention. Sensing the vitreous levels of desired sensed materials can be used to monitor and assess ocular processes as well as processes elsewhere in the body, such as the metabolic state of a patient or exposure to systemic drugs or locally administered drugs. A sensor composition of the invention can also be useful in personalized medicine for therapeutic drug monitoring as described, for example, in Griss et al.; 2014, *Nature Chemical Biology*, published online Jun. 8, 2014, DOI: 10.1038/NCHEMBIO.1554, the contents of which are incorporated by reference in its entirety. The compositions are also useful in research to monitor the status of an animal's physiologic state during experimental manipulations.

Accordingly, the invention provides a method of monitoring analytes in the eye. Such methods are useful, for example, to facilitate pharmacokinetic studies of therapeutic drugs injected into the eye, applied topically to the eye, or reaching the eye through systemic administration.

Hyaluronan (HA) Binding Peptide Tags

The term "hyaluronan" or "hyaluronic acid" or "HA" refers to a large polymeric glycosamine containing repeating disaccharide units of N-acetyl glucosamine and glucuronic acid that occurs in extracellular matrix and on cell surfaces. Hyaluronan is further described in J. Necas, L. Bartosikova, P. Brauner, J. Kolar, *Veterinarni Medicina*, 53, 2008 (8): 397-411.

The term "hyaladherin" or "hyaluronan binding proteins" or "HA binding proteins" refers to a protein or a family of proteins that bind hyaluronan. Examples of putative HA binding proteins are known in the art (Day, et al. 2002 *J Bio. Chem* 277:7, 4585 and Yang, et al. 1994, *EMBO J* 13:2, 286-296) (e.g.: Link, CD44, RHAMM, Aggrecan, Versican, bacterial HA synthase, collagen VI, and TSG-6). Many putative HA binding proteins, and peptide fragments, contain a common structural domain of ~100 amino acids in length involved in HA binding; the structural domain is referred to as a "LINK Domain" (Yang, et al. 1994, *EMBO J* 13:2, 286-296 and Mahoney, et al, 2001, *J Bio. Chem* 276:25, 22764-22771). For example, the LINK Domain of TSG-6, an HA binding protein, includes amino acid residues 36-128 of the human TSG-6 sequence.

In certain embodiments, a composition of the invention comprises at least one hyaluronan (HA) binding peptide that specifically binds hyaluronan in the eye. Hyaluronan is present in the body in various sizes in many organs in tissues. For example, the human eye and synovial fluid contain the highest concentrations of hyaluronan with 0.14-0.338 mg/ml in the vitreous and 1.42-3.6 mg/ml in joints, respectively, while other tissues and fluids contain much lower concentrations of hyaluronan such as serum in which hyaluronan concentrations are 0.00001-0.0001 mg/ml (Laurent and Fraser, 1986 Ciba Found Symp. 1986; 124:9-29). Non-ocular hyaluronan mainly consists of low molecular weight polymers that are rapidly degraded and turned over. In humans, hyaluronan has a half-life of 2.5-5 minutes in blood (Fraser J R, Laurent T C, Pertoft H, Baxter E. Biochem J. 1981 Nov. 15; 200(2):415-24.). In contrast, ocular hyaluronan mainly consists of high molecular weight polymers ($>0.5 \times 10^5$ daltons) and has a slower turnover rate of days or weeks (Laurent and Fraser, Exp. Eye Res. 1983; 36, 493-504). Due to these differences in the size and turnover of hyaluronan in the eye, the hyaluronan in the eye would serve as a sustained release scaffold for intravitreal proteins and nucleic acids linked to an HA-binding peptide.

Putative hyaluronan binding proteins have been described in the art (J. Necas, L. Bartosikova, P. Brauner, J. Kolar. Veterinarni Medicina, 53, 2008 (8): 397-411); examples are tumor necrosis factor-inducible gene 6 protein (TSG6), hyaluronan mediated motility receptor (RHAMM), CD44 antigen, hyaluronan and proteoglycan link protein 4, neurocan core protein, atabilin-2, and human glial hyaluronate-binding protein. However, the HA-binding domains of several putative hyluronan binding proteins tested did not bind HA, and they failed to increase the ocular half-life of proteins or nucleic acids linked to the putative HA-binding peptides. The present invention is based on the surprising discovery of peptides that effectively bind HA in the eye. This discovery prompted the secondary discovery that their use would delineate the vitreous when linked to a suitable optically detectable moiety, and thus would be suitable for facilitating ocular surgery where it is advantageous to visualize the vitreous, such as during a vitrectomy, or for use as long-lasting biosensors in the vitreous in the eye.

In certain aspects of the invention the peptide tag binds HA in the eye with a KD of less than or equal to 100 μM, 90 μM, 80 μM, 70 μM, 60 μM, 50 μM, 40 μM, 30 μM, 20 μM, or 10 μM. In particular, a composition of the invention can bind HA in the eye with a KD of less than or equal to 9.0 μM, less than or equal to 8.5 μM, less than or equal to 8.0 μM, less than or equal to 7.5 μM, less than or equal to 7.0 μM, less than or equal to 6.5 μM, less than or equal to 6.0 μM, less than or equal to 5.5 μM, less than or equal to 5.0 μM, less than or equal to 4.5 μM, less than or equal to 4.0 μM, less than or equal to 3.5 μM, less than or equal to 3.0 μM, less than or equal to 2.5 μM, less than or equal to 2.0 μM, less than or equal to 1.5 μM, less than or equal to 1.0 μM, less than or equal to 0.5 μM, or less than or equal to 100 nM. In more specific aspects, for example, the peptide binds HA in the eye with a KD of less than or equal to 8.0 μM, less than or equal to 7.2 μM, less than or equal to 6.0 μM, or less than or equal to 5.5 μM. In some aspects of the invention the peptide that binds HA has a LINK domain. In certain other aspects of the invention the LINK domain is a TSG-6 LINK domain. Modified versions of the peptide that also resist proteolytic cleavage and/or glycosylation can be utilized, or that facilitate manufacture of the peptides. More specifically the invention may include a peptide that binds, or is capable of binding, HA comprising a sequence of SEQ ID NO: 1, 2, 3, 4, 5, 6, 7, 8, 9, 10, 11, 12, or 13. It is contemplated that the peptide comprising a sequence of SEQ ID NO: 1, 2, 3, 4, 5, 6, 7, 8, 9, 10, 11, 12, or 13, binds, or is capable of binding, HA in the eye of a subject. It is contemplated that the peptide may be any one of the peptides listed in Table 1. More specifically, the peptide may be HA10, HA10.1, HA10.2, HA11, HA11.1, HA 10.1.1, NVS-A, NVS-X, NVS-Y, NVS-AX, NVS-AY, HA 11.APP (MBG100), or HA 11.HIS (MBG103). HA-binding peptides useful in a composition of the invention are also described in U.S. application Ser. No. 14/109,426, the entire contents of which are incorporated by reference.

In certain embodiments, the HA-binding peptide is or comprises the underlined portion of sequences in SEQ ID NOs: 6, 12, or 13.

TABLE 1

| | | Sequences |
|---|---|---|
| SEQ ID NO: 1 | Protein 1 (HA10) | GVYHREARSGKYKLTYAEAKAVCEFEGGHLA TYKQLEAARKIGFHVCAAGWMAKGRVGYPIV KPGPNCGFGKTGIIDYGIRLNRSERWDAYCY NPHAK |
| SEQ ID NO: 2 | Protein 2 (HA10.1) | GVYHREAQSGKYKLTYAEAKAVCEFEGGHL ATYKQLEAARKIGFHVCAAGWMAKGRVGYPI VKPGPNCGFGKTGIIDYGIRLNRSERWDAYC YNPHA |
| SEQ ID NO: 3 | Protein 3 (HA10.2) | GVYHREAASGKYKLTYAEAKAVCEFEGGHLA TYKQLEAARKIGFHVCAAGWMAKGRVGYPIV KPGPNCGFGKTGIIDYGIRLNRSERWDAYCY NPHA |
| SEQ ID NO: 4 | Protein 4 (HA11) | ACGVYHREAQSGKYKLTYAEAKAVCEFEGG HLATYKQLECARKIGFHVCAAGWMAKGRVG YPIVKPGPNCGFGKTGIIDYGIRLNRSERWDA YCYNPHA |
| SEQ ID NO: 5 | Protein 5 (HA11.1) | GVYHREAQSGKYKLTYAEAKAVCEFEGGHL CTYKQLEAARKIGFHVCAAGWMAKGRVGYPI VKPGPNCGFGKTGIIDYGIRLNRSERWDAYC CNPHA |
| SEQ ID NO: 6 | Protein 6 (HA10.1.1) | GGGGGGSGGG<u>GVYHREAQSGKYYLTYAEA KAVCEFEGGHLATYKQLEAARKIGFHVCAAG WMAKGRVGYPIVKPGPNCGFGKTGIIDYGIRL NRSERWDAYCYNPHA</u>GGSHHHHHH |
| SEQ ID NO: 7 | Protein 7 NVS-A | ACGVYHREAQSGKYKLTYAEAKAVCEFEGG HLATYKQLECARKIGFHVCAAGVVMAKGRVG YPIVKPGPNCGFGKTGIIDYGIRLNRSERWDA YCYNPHA |
| SEQ ID NO: 8 | Protein 8 NVS-X | GVYHREAISGKYYLTYAEAKAVCEFEGGHLA TYKQLLAAQKIGFHVCAAGVVMAKGRVGYPIV KPGPNCGFGKTGIIDYGIRLNRSERWDAYCY NPHA |
| SEQ ID NO: 9 | Protein 9 NVS-Y | GVYHREAISGKYYLTYAEAKAVCEFEGGHLA TYKQLQAAQKIGFHVCAAGWMAKGRVGYPIV KPGPNCGFGKTGIIDYGIRLNRSERWDAYCY NPHA |
| SEQ ID NO: 10 | Protein 10 NVS-AX | ACGVYHREAISGKYYLTYAEAKAVCEFEGGH LATYKQLLAAQKIGFHVCAAGWMAKGRVGY PIVKPGPNCGFGKTGIIDYGIRLNRSERWDAY CYNPHA |

TABLE 1-continued

Sequences

| SEQ ID NO: 11 | Protein 11 NVS-AY | ACGVYHREAISGKYYLTYAEAKAVCEFEGGH LATYKQLQAAQKIGFHVCAAGWMAKGRVGY PIVKPGPNCGFGKTGIIDYGIRLNRSERWDAY CYNPHA |
| --- | --- | --- |
| SEQ ID NO: 12 | Protein 12 (HA11 APP) MBG100 | GGGGGGSGGG*ACGVYHREAQSGKYYLTYA EAKAVCEFEGGHLATYKQLECARKIGFHVCA AGWMAKGRVGYPIVKPGPNCGFGKTGIIDYG IRLNRSERWDAYCYNPHAGGSEFRHDS* |
| SEQ ID NO: 13 | Protein 13 (HA11 HIS) MBG103 | GGGGGGSGGG*ACGVYHREAQSGKYYLTYA EAKAVCEFEGGHLATYKQLECARKIGFHVCA AGWMAKGRVGYPIVKPGPNCGFGKTGIIDYG IRLNRSERVVDAYCYNPHAGGS*HHHHHH |
| SEQ ID NO: 14 | DNA of SEQ ID NO: 1 (HA10) | GGAGTCTATCACAGAGAGGCTAGATCAGG CAAGTATAAGCTGACCTACGCCGAGGCTAA GGCCGTGTGCGAGTTCGAGGGCGGTCACC TGGCTACCTATAAGCAGCTGGAAGCCGCTA GAAAGATCGGCTTTCACGTGTGCGCCGCT GGCTGGATGGCTAAGGGTAGAGTGGGCTA CCCTATCGTGAAGCCTGGCCCTAACTGCG GCTTCGGTAAAACCGGAATTATCGACTACG GGATTAGGCTGAATAGATCAGAGCGCTGG GACGCCTACTGCTATAACCCTCACGCTAAG |
| SEQ ID NO: 15 | DNA of SEQ ID NO: 2 (HA10.1) | GGAGTCTATCACAGAGAGGCTCAGTCAGG CAAGTATAAGCTGACCTACGCCGAGGCTAA GGCCGTGTGCGAGTTCGAGGGCGGTCACC TGGCTACCTATAAGCAGCTGGAAGCCGCTA GAAAGATCGGCTTTCACGTGTGCGCCGCT GGCTGGATGGCTAAGGGTAGAGTGGGCTA CCCTATCGTGAAGCCTGGCCCTAACTGCG GCTTCGGTAAAACCGGAATTATCGACTACG GGATTAGGCTGAATAGATCAGAGCGCTGG GACGCCTACTGCTATAACCCTCACGCC |
| SEQ ID NO: 16 | DNA of SEQ ID NO: 3 (HA10.2) | GGAGTCTATCACAGAGAGGCTGCTAGCGG TAAATACAAGCTGACCTACGCCGAGGCTAA GGCCGTGTGCGAGTTCGAGGGCGGTCACC TGGCTACCTATAAGCAGCTGGAAGCCGCTA GAAAGATCGGCTTTCACGTGTGCGCCGCT GGCTGGATGGCTAAGGGTAGAGTGGGCTA CCCTATCGTGAAGCCTGGCCCTAACTGCG GCTTCGGTAAAACCGGAATTATCGACTACG GGATTAGGCTGAATAGATCAGAGCGCTGG GACGCCTACTGCTATAACCCTCACGCC |
| SEQ ID NO: 17 | DNA of SEQ ID NO: 4 (HA11) | GGCGCCTGTGGCGTGTATCACAGGGAGGC CCAGAGCGGCAAGTACAAGCTCACCTACG CCGAGGCCAAGGCCGTGTGCGAATTCGAG GGCGGCCACCTGGCCACCTACAAGCAGCT GGAGTGCGCCAGGAAGATCGGCTTCCACG TGTGTGCCGCCGGCTGGATGGCCAAAGGC AGAGTGGGCTACCCCATCGTGAAACCCGG CCCCAACTGCGGCTTCGGCAAGACAGGCA TCATCGACTACGGCATCAGGCTGAACAGGA GCGAGAGGTGGGACGCCTACTGCTACAAC CCCCACGCC |
| SEQ ID NO: 18 | DNA of SEQ ID NO: 5 (HA11.1) | GGAGTGTATCACAGAGAGGCCCAGAGCGG CAAGTACAAGCTGACCTACGCCGAGGCCA AGGCCGTGTGTGAGTTCGAGGGCGGCCAC CTGTGCACCTACAAGCAGCTGGAGGCCGC CAGGAAGATCGGCTTCCACGTGTGTGCCG CCGGCTGGATGGCTAAAGGCAGGGTGGGC TACCCCATTGTGAAGCCCGGCCCCAATTGC GGCTTCGGCAAGACCGGCATCATCGACTA CGGCATCAGGCTGAACAGGAGCGAGAGGT GGGACGCCTACTGCTGCAACCCCCACGCC |

In certain aspects, the peptide can have a sequence comprising 30, 35, 40, 45, 50, 55, 60, 65, 70, 75, 80, 85, 90, 91, 92, 93, 94, 95, 96, 97 or 98 consecutive amino acids of SEQ ID NOs: 1, 2, 3, 4, 5, 6, 7, 8, 9, 10, 11, 12, or 13. In certain other aspects, it is contemplated that a peptide is a truncated variant of a peptide comprising a sequence of SEQ ID NO: 1, 2, 3, 4, 5, 6, 7, 8, 9, 10, 11, 12, or 13. Amino acids may be cleaved from the N-terminus, C-terminus or both of the peptide comprising a sequence of SEQ ID NO: 1, 2, 3, 4, 5, 6, 7, 8, 9, 10, 11, 12, or 13 to produce a truncated variant of the peptides HA10, HA10.1, HA10.2, HA11, HA11.1, NVS-A, NVS-X, NVS-Y, NVS-AX, NVS-AY, HA 11.APP (MBG100), or HA 11.HIS (MBG103). It is further contemplated that the sequence may be cleaved from the N-terminus of SEQ ID NO: 1, 2, 3, 4, 5, 6, 7, 8, 9, 10, 11, 12, or 13 up to and (but not including) the first N-terminal cysteine. It is further contemplated that the sequence may be cleaved from the C-terminus of SEQ ID NO: 1, 2, 3, 4, 5, 6, 7, 8, 9, 10, 11, 12, or 13 up to and (but not including) the first C-terminal cysteine. It is further contemplated that the sequence may be cleaved from both the N-terminus and the C-terminus of SEQ ID NO: 1, 2, 3, 4, 5, 6, 7, 8, 9, 10, 11, 12, or 13 up to (but not including) the first N-terminal cysteine and (but not including) the first C-terminal cysteine. For example, with respect to SEQ ID NO: 1, one of skill in the art could remove up to 22 amino acids from the N-terminal end (bold) and/or up to six amino acids from the C-terminal end (underline):

(SEQ ID NO: 1)
GVYHREARSGKYKLTYAEAKAVCEFEGGHLATYKQLEAARKIGFHVCAAG
WMAKGRVGYPIVKPGPNCGFGKTGIIIDYGIRLNRSERWDAYC<u>YNPHAK</u>.

In certain aspects of the invention it is contemplated that a single peptide is linked to an optically detectable moiety. In other aspects of the invention it is contemplated that two, three, four or more peptide tags maybe linked to the optically detectable moiety. In other aspects of the invention it is contemplated that two, three, four, or more optically detectable moieties may be linked to one HA-binding peptide.

Production

The HA-binding peptide can be linked to an optically detectable moiety using conventional methods known to those skilled in the art. For example, an HA-binding peptide can be expressed by transient transfection of mammalian expression vector in HEK293 cells and purified using standard affinity resins and conjugated with a fluorophore as described herein below.

The present invention provides peptides that can be recombinantly fused (i.e., linked) or chemically conjugated (including both covalent and non-covalent conjugations) to other molecules such as fluorophores, chromophores, protein biosensors, other proteins, or nucleic acids. In certain aspects the peptide binds HA. In other aspects, the peptide binds HA and comprises a LINK Domain. In other aspects, the peptide binds HA and comprises a TSG-6 LINK Domain. More specifically, it is contemplated that the peptide may be HA10 (SEQ ID NO: 1), HA10.1 (SEQ ID NO: 2), HA10.2 (SEQ ID NO: 3), HA11 (SEQ ID NO: 4) or HA11.1 (SEQ ID NO: 5), HA 10.1.1 (SEQ ID NO: 6), NVS-A (SEQ ID NO: 7), NVS-X (SEQ ID NO: 8), NVS-Y (SEQ ID NO: 9), NVS-AX (SEQ ID NO: 10), NVS-AY (SEQ ID NO: 11), HA 11.APP (MBG100) (SEQ ID NO: 12), or HA 11.HIS (MBG103) (SEQ ID NO: 13). The peptide can also be a peptide described in U.S. application Ser. No. 14/109,426, the entire contents of which are hereby incorporated by reference.

Standard molecular biology techniques can be used to prepare and express an HA-binding peptide or peptide sequences to be used in a composition of the invention.

Moreover, the HA-binding peptides can be fused to small peptide sequences to facilitate manufacture and purification. For example, the marker amino acid sequence is a hexa-histidine peptide (SEQ ID NO: 19), such as the marker provided in a pQE vector (QIAGEN®, Inc., 9259 Eton Avenue, Chatsworth, Calif., 91311), among others, many of which are commercially available. As described in Gentz et al., 1989, Proc. Natl. Acad. Sci. USA 86:821-824, for instance, hexa-histidine (SEQ ID NO: 19) provides for convenient purification of the fusion protein. Other small peptides useful for purification include, but are not limited to, the hemagglutinin tag, which corresponds to an epitope derived from the influenza hemagglutinin protein (Wilson et al., 1984, Cell 37:767), and the "flag" tag.

Delivery

The invention provides compositions comprising a peptide of the invention, for example a peptide that binds HA in the eye with a KD of less than or equal to 100 µM, 90 µM, 80 µM, 70 µM, 60 µM, 50 µM, 40 µM, 30 µM, 20 µM, 10 µM, 9.0 µM, 8.5 µM, 8.0 µM, 7.5 µM, 7.0 µM, 6.5 µM, 6.0 µM, 5.5 µM, 5.0 µM, 4.5 µM, 4.0 µM, 3.5 µM, 3.0 µM, 2.5 µM, 2.0 µM, 1.5 µM, 1.0 µM, or 0.5 µM. In certain specific aspects the peptide may comprise the sequence of SEQ ID NO: 1, 2, 3, 4, 5, 6, 7, 8, 9, 10, 11, 12, or 13, formulated together, or separately, with a pharmaceutically acceptable excipient, diluent or carrier. The invention also provides compositions comprising HA tagged optically detectable moiety molecules (e.g., a peptide linked to an optically detectable moiety), formulated together, or separately, with a pharmaceutically acceptable excipient, diluent or carrier.

In certain aspects the compositions of the invention comprise a peptide that binds HA in the eye as described above. The compositions can additionally contain one or more therapeutic agents that are suitable for treating or preventing, for example, conditions or disorders associated with retinal vascular disease or useful in surgery, such as anti-inflammatory, anti-scarring, and wound healing agents. Pharmaceutically acceptable carriers enhance or stabilize the composition, or can be used to facilitate preparation of the composition. Pharmaceutically acceptable carriers include solvents, dispersion media, coatings, antibacterial and antifungal agents, isotonic and absorption delaying agents, and the like that are physiologically compatible. The pharmaceutically acceptable excipient, diluent or carrier should be suitable for administration to the eye (e.g., by injection, subconjunctival or topical administration), more specifically, for intravitreal administration. The invention also provides for methods of producing a composition for ocular delivery wherein the method includes the step of linking a peptide that binds HA in the eye with a KD of less than or equal to 100 µM, 90 µM, 80 µM, 70 µM, 60 µM, 50 µM, 40 µM, 30 µM, 20 µM, 10 µM, 9.0 µM, 8.5 µM, 8.0 µM, 7.5 µM, 7.0 µM, 6.5 µM, 6.0 µM, 5.5 µM, 5.0 µM, 4.5 µM, 4.0 µM, 3.5 µM, 3.0 µM, 2.5 µM, 2.0 µM, 1.5 µM, 1.0 µM, or 0.5 µM to an optically detectable moiety (e.g., a fluorophore or chromophore), and is useful for visualizing the vitreous.

In certain embodiments, the compositions of the invention can be incorporated into vesicles which provide a suitable ophthalmic injectable. Examples of such vesicles include liposomes or microspheres, for example, poly(glycolic) or poly(lactic) acid microspheres. Incorporation of compositions into liposomes or microspheres can be performed by routine procedures as known to one skilled in the art.

A composition of the present invention can be administered by a variety of methods known in the art. The route and/or mode of administration vary depending upon the desired results. It is preferred that the composition be suitable for administration to the eye, more specifically, the composition may be suitable for intravitreal administration.

A formulation comprising a composition of the invention should be sterile and fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

Compositions of the invention for administration to the eye can be prepared in accordance with methods well known and routinely practiced in the art See, e.g., Remington: The Science and Practice of Pharmacy, Mack Publishing Co., 20th ed., 2000. Pharmaceutical compositions are preferably manufactured under GMP conditions.

In certain embodiments, a composition of the invention is injected into a mammalian eye in an aqueous solution of about 150 μl or less, and the solution comprises at least about 0.001 μg of the composition. In certain embodiments, the solution is formulated to deliver about 0.001 μg, 0.01 μg, 0.1 μg, 1.0 μg, 10 μg, 20 μg, 30 μg, 40 μg, 50 μg, 60 μg, 70 μg, 80 μg, 90 μg, 100 μg, 200 μg, 300 μg, 400 μg, 500 μg, 600 μg, 700 μg, 800 μg, 900 μg, 1.0 mg, 2.0 mg, 3.0 mg, 4.0 mg, or about 5.0 mg of a composition of the invention per injection. In certain embodiments, the solution is formulated to deliver less than about 1.0 mg of a composition of the invention per injection. In certain embodiments, the volume of the aqueous solution is about 1.0 μl to about 150 μl, preferably about 20 μl to about 100 μl.

The invention will be further appreciated in light of the following examples.

EXAMPLES

The following Examples are provided for the purposes of illustration and are not intended to limit the scope of the present invention. The present invention is not to be limited in scope by the exemplified embodiments, which are intended as illustrations of individual aspects of the invention. Indeed, various modifications of the invention in addition to those shown and described herein will become apparent to those skilled in the art from the foregoing description and accompanying drawings. Such modifications are intended to fall within the scope of the appended claims.

Example 1: HA-Tagged Chromophore Visualization of the Vitreous

A FITC linked HA-binding protein was generated as follows.
Expression and Purification:

An HA-binding peptide (Protein 6 in Table 1) was transiently expressed in HEK293F cells using polyethylenimine (PEI) as transfection agent with ratio of 1:3 of plasmid DNA to PEI and grown for five days at 37° C. with 5% $CO_2$. The culture was harvested and the supernatant filtered. The conditioned medium was loaded onto nickel resin column, washed with 50 mM phosphate buffer containing 20 mM immidazole, 500 mM sodium chloride, pH 8 to remove unbound proteins, and gradient eluted with 50 mM phosphate buffer containing 500 mM imidazole, 500 mM sodium chloride, pH 8.

The purified Protein 6 was site-specifically labeled with fluorescein isothiocyanate on the N-terminus using Sortase-A mediated reaction (see Mao et al., 2004, *J Am Chem Soc.*, March 10;126(9):2670-1). The fluorophore (fluorescein isothiocyanate)—conjugated HA-binding peptide was purified to apparent homogeneity using standard mixed mode and ion exchange resins. Specifically, Protein 6 was buffer exchanged into Sortase labeling buffer (50 mM Tris-HCl, 150 mM sodium chloride, 10 mM CaCl2, pH 7.5). Reaction mix in the Sortase labeling buffer contained 50 uM of Protein 6, 2 mM of FITC-LPETGGG (SEQ ID NO: 20) (synthesized by GeneScript) and ~150 uM of Sortase A immobilized on agarose in the sortase labeling buffer. The reaction mix was incubated at 23° C. for 24 hours with shaking. The immobilized Sortase A was separated using 0.2 μm filter. The pH of the flowthrough containing labeled and unlabeled Protein 6 was increased to pH 9 with 1M Tris-HCl, pH 9.5. The sample was then loaded over a 5 mL CaptoAdhere column, washed with PBS, pH 7.4, and eluted with gradient of 100 mM citrate buffer, pH 3. Eluted fractions were neutralized with 1/10 volume 1M Tris-HCl, pH 9.5. The fractions were run on SDS-PAGE gel and imaged under fluorescence mode. The final labeled protein was buffer exchanged into PBS, pH 7.4.

Animals and Treatment Regimen

The animals used in this example were male Rabbit/New Zealand White×New Zealand Red. The treatment regimen used is shown in the following Table 2.

TABLE 2

| Group No. | Test Article (Dose) | Dosing Regimen | | |
|---|---|---|---|---|
| | | Animals per Group | Volume/Injection (μL)[a] | Total Doses |
| 1 | FITC-PROTEIN 6 2.5 μg total protein/injection | 3 | 50 | 1 |
| 2 | FITC-PROTEIN 6 5 μg total protein/injection | 3 | 50 | 1 |

[a]administered by intravitreal injection, OU (both eyes)

The study evaluations and frequency are described in Table 3.

TABLE 3

| Evaluations | Frequency |
|---|---|
| Clinical Observations | Prescreen |
| Morbidity/Mortality Check | Study Days 1, 2 and 3 |
| Body weights | Prescreen |
| IVT injections OU | Study Day 1 |
| Wide angle imaging | Prescreen, post injection, 16 hr, 24 hr, approximately 48 hr and approximately 72 hr |
| Fluorophotometry | Prescreen, post injection, 16 hr, 24 hr, approximately 48 hr and approximately 72 hr |

OU = both eyes

Heidelberg Retina and Vitreous Images:

Non-invasive BluePeak™—Blue laser Autofluorescence Imaging Mode in Spectralis® from Heidelberg Engineering, Inc, was used to obtain wide angle photographs of vitreous chamber/retina. A wide angle contact lens (Staurenghi 150° contact lens) with a methylcellulose transmission gel placed in contact with the cornea was used to aid visualization of the posterior segment of the eye. The eyelid was retracted; the contact lens was placed on the cornea and positioned in front of the camera by a trained technician.

Fluorophotometry

Fluorophotometry measures the concentration of a fluorescent compound, typically fluorescein, along the optical axis of the eye from the tear film to the retina. The eyelids were retracted and the animal was placed in front of the Fluorotron Master by a trained technician. Fluorescein content was then quantified by the fluorophotometer without making contact with the eye. Two to three scans were performed for each eye at each time point. The average from these repeated scans of each individual eye at each time point was used for further analysis.

Intravitreal Injection

An operating microscope was used to visualize the posterior segment of the eye during the procedure. The eyelid was retracted with a wire speculum. The globe was immobilized using ocular forceps. A 30-gauge needle attached to a sterile syringe, containing the test article, was passed through the sclera 3 to 5 mm posterior to the temporal limbus and angled posterior to avoid the lens. The target location of the injection was the superior-temporal region.

Care of animals, including pain management, was in compliance with global animal welfare requirements.

Results:

Microscopic Visualization (Operating Microscope)

The test article was observed in the vitreous of the animals by microscopic visualization immediately post-injection at both doses (2 and 5 ug). The color was apparent under standard illumination from the operating microscope without the need for excitation or emission filters. Microscopic visualization at other time-points was not conducted.

Figure 5A:
FIG. 5A is a photo of a rabbit eye using autofluorescence wide angle imaging and 80% gain 24 hours after being injected with a composition 2.5 µg of the invention.
Figure 5B:
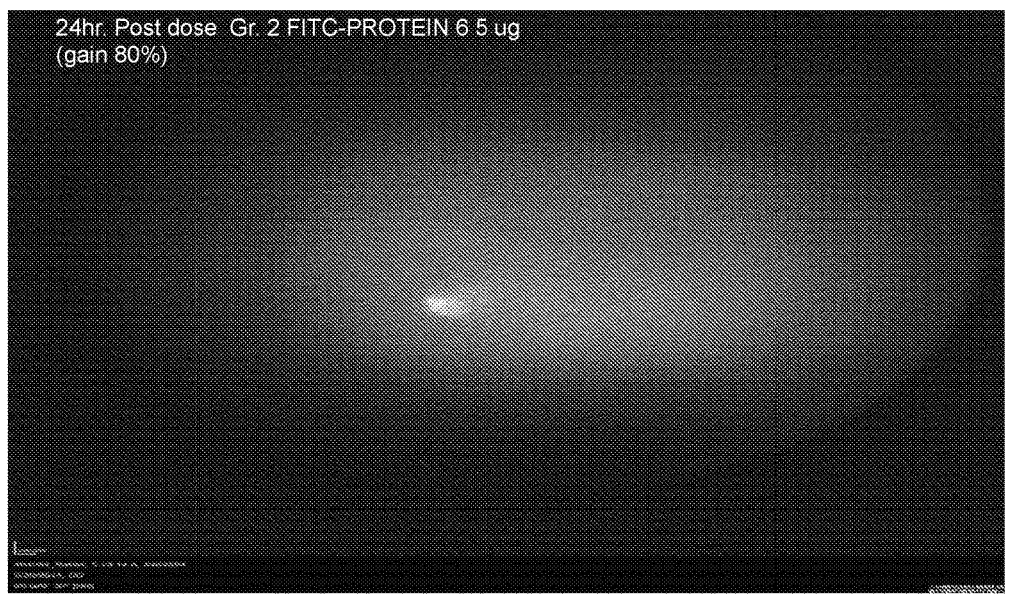
FIG. 5B is a photo of a rabbit eye using autofluorescence wide angle imaging and 80% gain 24 hours after being injected with 5 µg of a composition of the invention.
Figure 6A:
FIG. 6A is a photo of a rabbit eye using autofluorescence wide angle imaging and 80% gain 48 hours after being injected with a composition 2.5 µg of the invention.
Figure 6B:
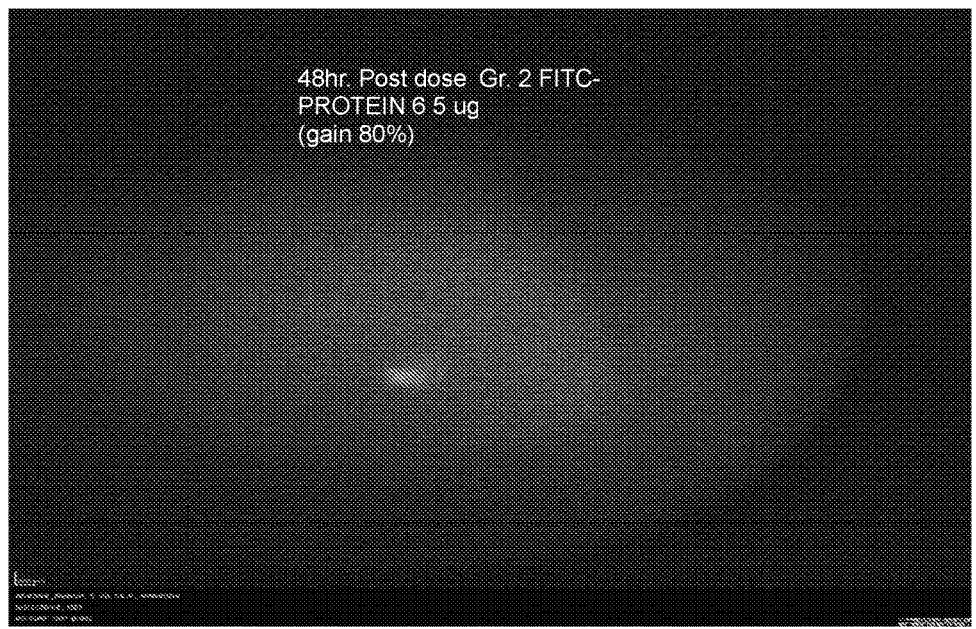
FIG. 6B is a photo of a rabbit eye using autofluorescence wide angle imaging and 80% gain 48 hours after being injected with 5 µg of a composition of the invention.

Heidelberg Retina and Vitreous Images:

Baseline images did not show any evidence of fluorescence. Post IVT injection, the test article from both dose groups diffused into the vitreous as seen by the wide angle images of the vitreous chamber. A small area of fluorescence was noted close to the injection site post injection for both dose groups. By 16 hours, the test article had dispersed further with the 5 µg dose (Group 2, FIG. 4B) eyes showing relatively higher fluorescence than the 2.5 µg dose (Group 1, FIG. 4A) eyes. The test article continued to be visible throughout the vitreous at 24, 48 and 72 hours in both dose groups (see FIGS. 5-7, respectively) with intensity fading after 24 hours. As expected, the 5 µg high dose group demonstrated higher fluorescence than the lower 2.5 µg dose (See FIGS. 4-7).

Fluorophotometry:

The fluorophotometer measures the fluorescence of the ocular tissue on a linear scan along the optical axis of the eye. A vitreous injection of fluorescein cannot be detected until the fluorescein enters the optical axis of the eye.

Figure 4A:
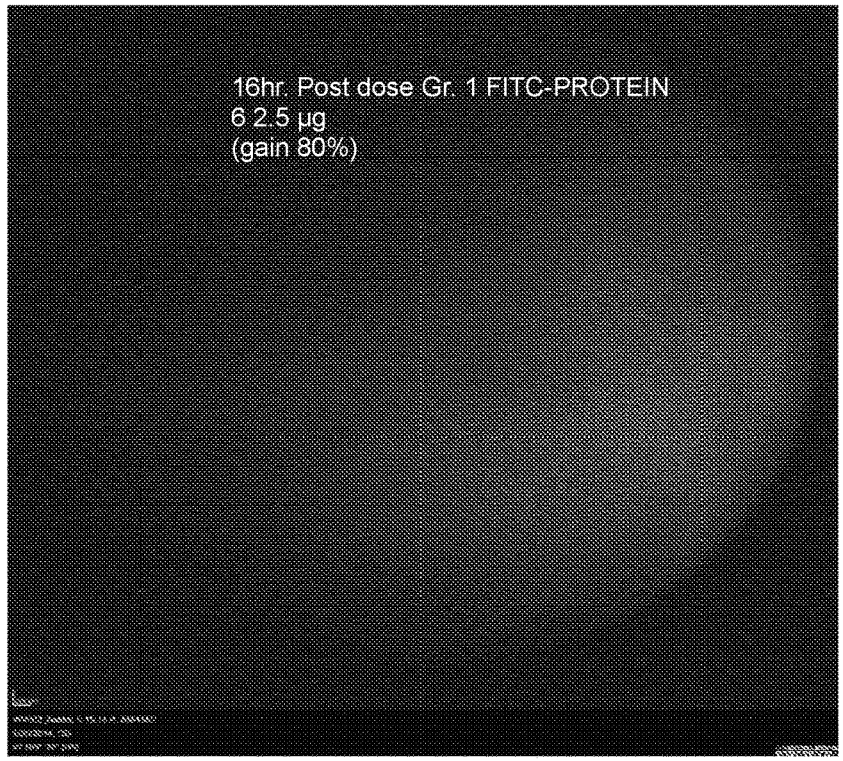
FIG. 4A is a photo of a rabbit eye using autofluorescence wide angle imaging and 80% gain 16 hours after being injected with 2.5 µg of a composition of the invention.
Figure 7A:
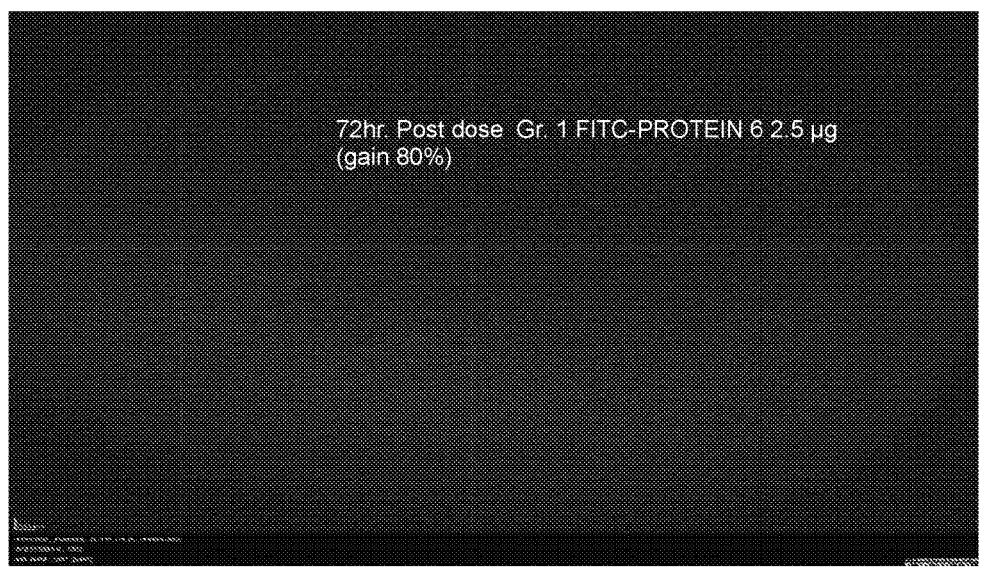
FIG. 7A is a photo of a rabbit eye using autofluorescence wide angle imaging and 80% gain 72 hours after being injected with a composition 2.5 µg of the invention.
Figure 7B:
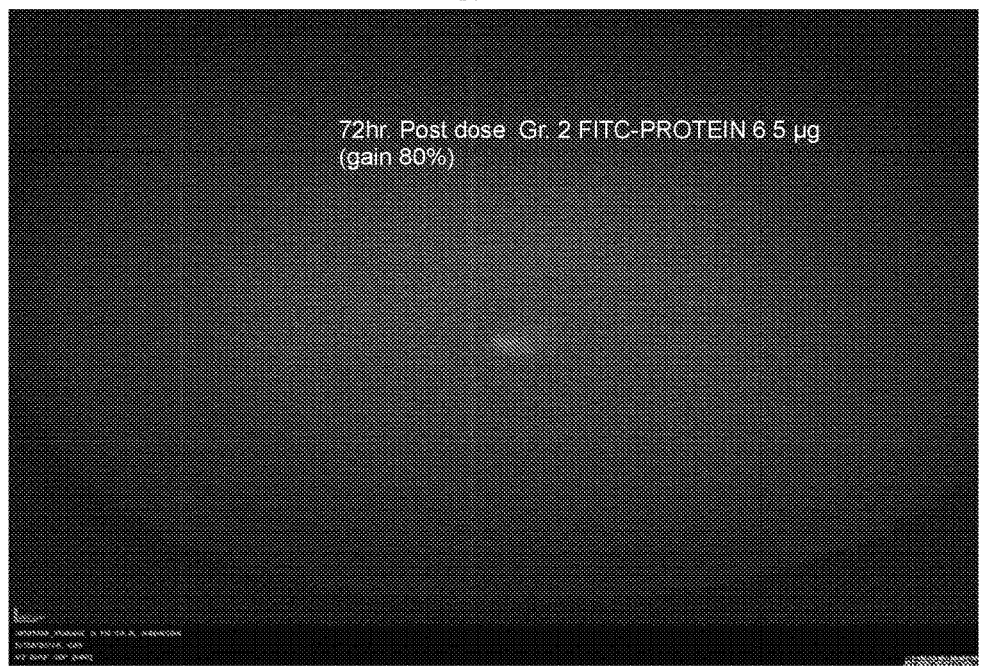
FIG. 7B is a photo of a rabbit eye using autofluorescence wide angle imaging and 80% gain 72 hours after being injected with 5 µg of a composition of the invention.

For the 2.5 µg dose group, fluorescence of the test article was first observed 16 h after injection in the vitreous cavity (FIG. 4A and FIG. 1). The relative fluorescence in the vitreous was also highest at this time point. The relative fluorescence in the vitreous was similar at the 24 hour time point (FIG. 5A and FIG. 1) with decreases observed at 48 hours (FIG. 6A and FIG. 1) and again at 72 hours (FIG. 7A and FIG. 1). No obvious change was noted in the fluorescence level in the anterior segment of the eye (from cornea to lens).

Figure 2:
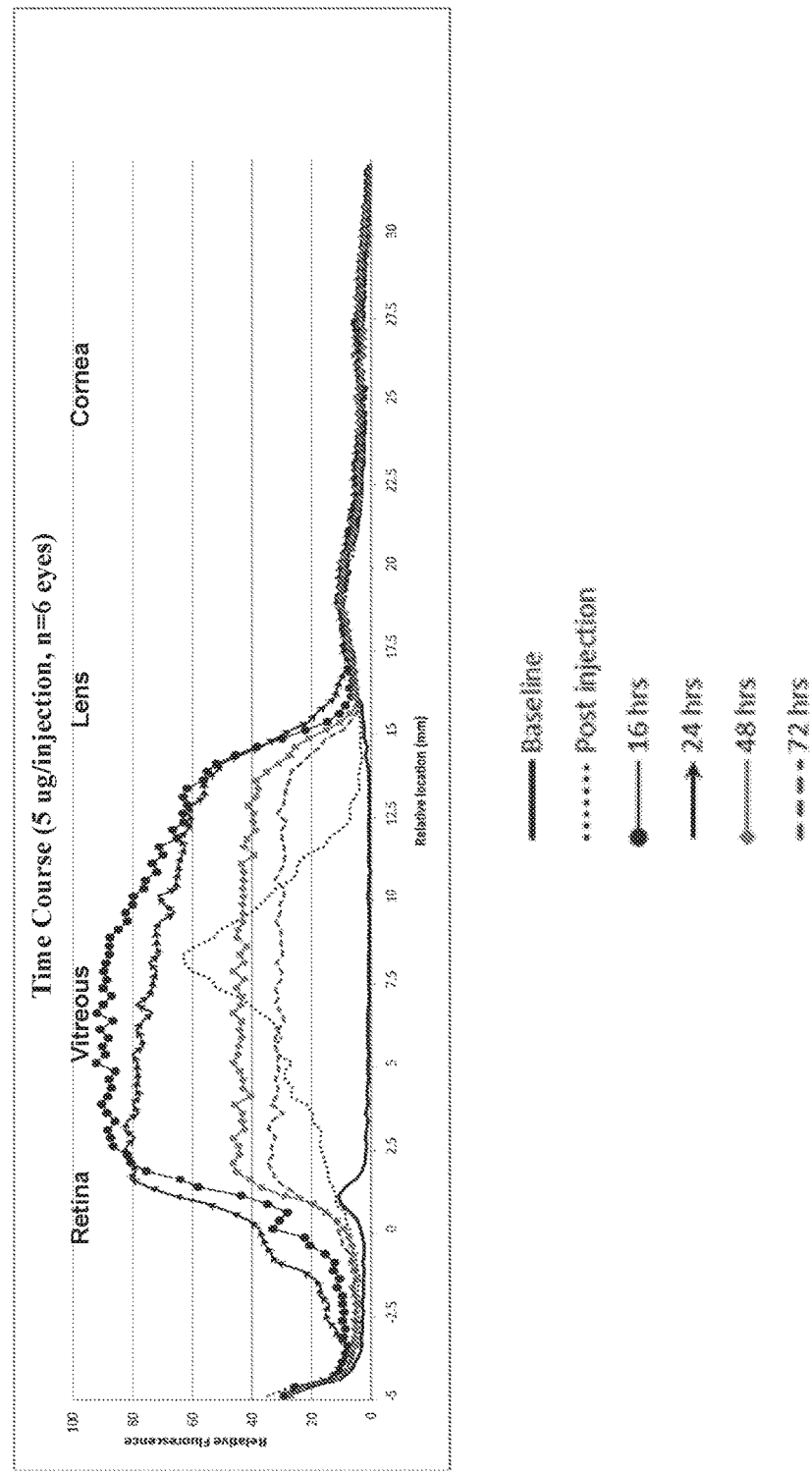
FIG. 2 demonstrates time related relative fluorescence change, especially in the vitreous body of rabbit eyes after IVT administration of a composition of the invention at 5 µg (mean value, n=6 eyes).
Figure 3A:
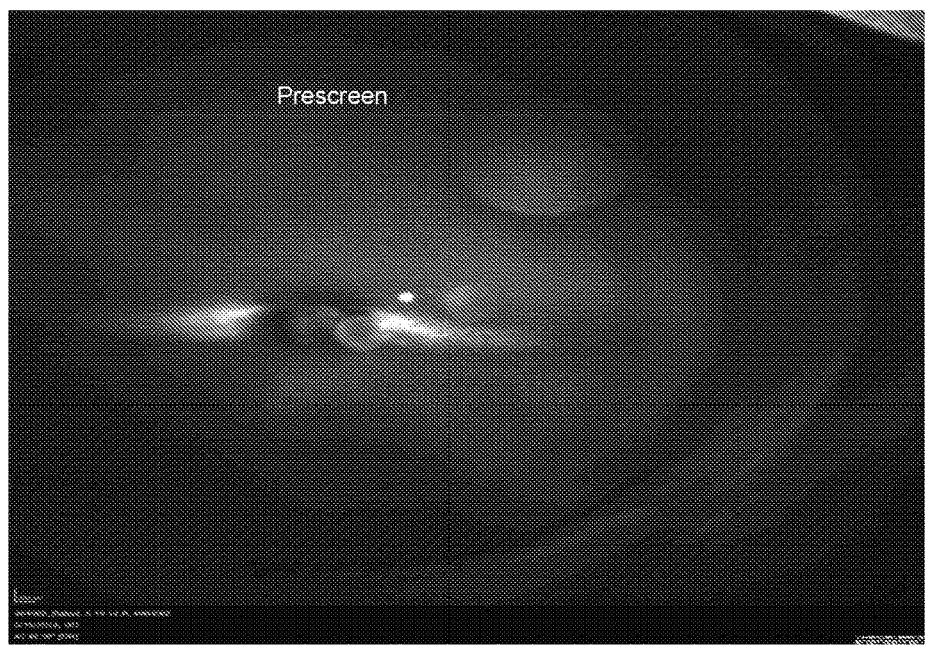
FIG. 3A is a photo of a rabbit eye before being injected with a composition of the invention.
Figure 3B:
FIG. 3B is a photo of a rabbit eye using autofluorescence wide angle imaging and 80% gain before being injected with a composition of the invention.
Figure 4B:
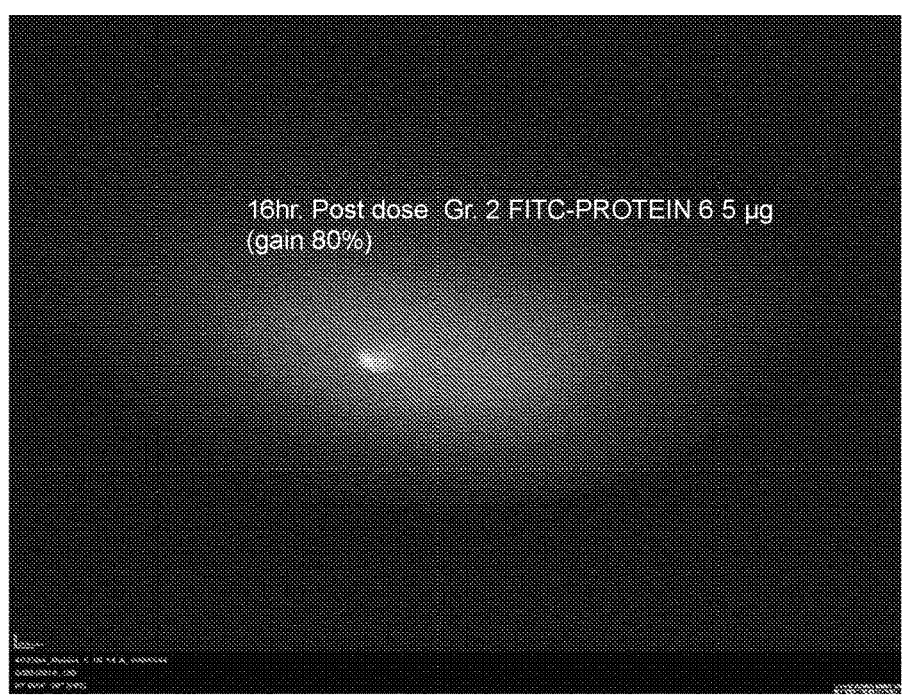
FIG. 4B is a photo of a rabbit eye using autofluorescence wide angle imaging and 80% gain 16 hours after being injected with 5 µg of a composition of the invention.

For the 5 µg dose group, relative fluorescence was detected in the vitreous post injection however, it was not evenly dispersed at this time. By 16 h, the fluorescence was better dispersed in the vitreous (FIG. 4B and FIG. 2). A similar trend of test article diffusion as seen with the 2.5 µg dose group was observed following the high dose 5 µg dose group except that the fluorescence was relatively higher than in the 2.5 µg group. Also, no obvious change was noted in the fluorescence level in the anterior segment of the eye (from cornea to lens).

SUMMARY

Chromophore conjugated hyaluronan-binding protein, FITC-Protein 6, a glycosylated protein, was injected into the vitreous and observed by wide angle imaging and fluorophotometry immediately post injection (only for the 5 µg dose group with fluorophotometry), and at 16 hr, 24 hr, approximately 48 hr and approximately 72 hr post-injection (see FIG. 4A, FIG. 5A, FIG. 6A, FIG. 7A, respectively for the 2.5 µg dose, and see FIG. 4B, FIG. 5B, FIG. 6B, FIG. 7B, respectively for the 5 µg dose). Complete vitreous diffusion of the test article was apparent by the 16 h post-injection observation for both dose groups. As expected, the high dose 5 µg group demonstrated higher fluorescence in the vitreous than the lower 2.5 µg dose. No obvious changes were noted in the fluorescence level in the anterior segment of the eye (from cornea to lens). This study demonstrated that FITC-Protein 6 diffused in the vitreous and also demonstrated the feasibility of visualizing of vitreous during vitrectomy surgery.

Example 2: Ocular Surgery

The composition of the invention is placed in a formulation suitable for intravitreal injection (i.e., with the appropriate pH, osmolarity, low endotoxin level, etc., that is customarily achievable by those skilled in the art of formulating drugs for intravitreal injection and demonstrated in the previously mentioned pilot research studies in rabbit eyes.) A few hours prior to surgery or even one to three days prior to surgery, the formulation containing the composition is injected into the vitreous. The volume of the dose would be in the range of 1 microliter to 100 microliters. As is standard for intravitreal injections, the injection site is a few mm posterior to the limbus so that the needle enters the eye at the pars plana. A vitreous delineating composition of the invention is injected about 5-10 mm deep into the vitreous.

As demonstrated in the pilot studies in Example 1 above, the composition diffuses throughout the vitreous within hours so that by 16 hours (and perhaps much sooner in eyes from older humans with vitreous syneresis) there is relatively uniform concentration of the composition across the entire vitreous cavity. As shown in Example 1, this diffusion and dispersion of the composition throughout the vitreous does not require any special manipulation of the eye; it is expected that it will occur in the course of the normal activities of a patient and the normal motion of a patient's eye. Once the vitreous gel is colored or fluorescent, the eye is ready for a surgical procedure. The vitreous is rendered visible by the chromophore itself in the white light of the operating microscope, or, alternatively, it would become fluorescent whenever the surgeon activates a standard light or laser light with the appropriate wavelength (hue) to generate a detectable signal from the composition.

Because the composition sticks to hyaluronic acid, it will not wash away during the rinsing of the vitreous with fluid as normally occurs during vitrectomy surgery. Instead, the composition will maintain its binding to hyaluronan, an essential component of vitreous. As the surgeon removes vitreous with surgical instruments as standard in such procedures, the regions of vitreous not yet removed are easily apparent by the color or fluorescence of a composition of the invention, which can be observed constantly or whenever the appropriate light is transiently switched on during the procedure. Because of the great difference in hyaluronan content in the vitreous compared to the inner retina and especially compared to the inner limiting membrane of the retina, the vitreous delineating composition of the invention clearly delineates the vitreoretinal interface and thus allows the surgeon to approach the retina with vitrectomy instruments only when necessary to remove the last remnants of vitreous.

The composition also facilitates recognition of a posterior vitreous detachment because of the clear fluid between the vitreous and the retina having a low hyaluronan content. The vitreous delineating composition of the invention binds to hyaluronan present in the posterior cortical vitreous, thus clearly distinguishing a boundary between the cortical vitreous and the fluid-filled posterior hyaloid space. The limit of the hyaloid is thus visibly demarcated by the vitreous delineating composition bound to the vitreous. This allows the surgeon to accurately visualize the posterior hyaloid and vitreous during the procedure, and to completely and easily remove the posterior hyaloid and formed vitreous. Complete removal can be confirmed by when no vitreous delineating composition remains on the surface of the retina.

It should be understood that the embodiments of the present invention shown and described in the specification are only preferred embodiments of the inventor who is skilled in the art and are not limiting in any way. Therefore, various changes, modifications or alterations to these embodiments may be made or resorted to without departing from the spirit of the invention and the scope of the following claims.

What is claimed is:

1. A method of visualizing the vitreous during vitrectomy surgery comprising:
injecting into an eye an inert composition comprising a peptide that binds hyaluronan that is linked to an optically detectable moiety in an amount effective to render the vitreous visible, wherein (i) the peptide comprises a sequence selected from the group consisting of: SEQ ID NO: 6 and 95 consecutive amino acids of the sequence of SEQ ID NO: 6, and (ii) the peptide is linked to fluorescein isothiocyanate.

2. The method of claim 1, wherein said composition is formulated as a vesicle selected from the group consisting of a liposome and a microsphere.

3. The method of claim 1, wherein said composition has a formulation selected from the group consisting of a solution, an emulsion, and a suspension.

4. A method of staining the vitreous in a mammalian eye comprising:
injecting a composition comprising a peptide linked to fluorescein isothiocyanate wherein the peptide comprises a sequence selected from the group consisting of SEQ ID NO: 6 and 95 consecutive amino acids of SEQ ID NO: 6 into the mammalian eye; and
applying an energy source selected from a light or laser to the eye to generate a signal from the fluorescein isothiocyanate.

* * * * *

```
                          SEQUENCE LISTING

<160> NUMBER OF SEQ ID NOS: 20

<210> SEQ ID NO 1
   <211> LENGTH: 98
   <212> TYPE: PRT
   <213> ORGANISM: Artificial Sequence
   <220> FEATURE:
   <221> NAME/KEY: source
   <223> OTHER INFORMATION: /note="Description of Artificial Sequence:
         Synthetic polypeptide"

<400> SEQUENCE: 1

Gly Val Tyr His Arg Glu Ala Arg Ser Gly Lys Tyr Lys Leu Thr Tyr
   1               5                   10                  15

Ala Glu Ala Lys Ala Val Cys Glu Phe Glu Gly Gly His Leu Ala Thr
               20                  25                  30

Tyr Lys Gln Leu Glu Ala Ala Arg Lys Ile Gly Phe His Val Cys Ala
           35                  40                  45

Ala Gly Trp Met Ala Lys Gly Arg Val Gly Tyr Pro Ile Val Lys Pro
       50                  55                  60

Gly Pro Asn Cys Gly Phe Gly Lys Thr Gly Ile Ile Asp Tyr Gly Ile
   65                  70                  75                  80

Arg Leu Asn Arg Ser Glu Arg Trp Asp Ala Tyr Cys Tyr Asn Pro His
                   85                  90                  95

Ala Lys

<210> SEQ ID NO 2
   <211> LENGTH: 97
   <212> TYPE: PRT
   <213> ORGANISM: Artificial Sequence
   <220> FEATURE:
   <221> NAME/KEY: source
   <223> OTHER INFORMATION: /note="Description of Artificial Sequence:
         Synthetic polypeptide"

<400> SEQUENCE: 2

Gly Val Tyr His Arg Glu Ala Gln Ser Gly Lys Tyr Lys Leu Thr Tyr
   1               5                   10                  15

Ala Glu Ala Lys Ala Val Cys Glu Phe Glu Gly Gly His Leu Ala Thr
               20                  25                  30

Tyr Lys Gln Leu Glu Ala Ala Arg Lys Ile Gly Phe His Val Cys Ala
           35                  40                  45

Ala Gly Trp Met Ala Lys Gly Arg Val Gly Tyr Pro Ile Val Lys Pro
       50                  55                  60
```

Gly Pro Asn Cys Gly Phe Gly Lys Thr Gly Ile Ile Asp Tyr Gly Ile
65                  70                  75                  80

Arg Leu Asn Arg Ser Glu Arg Trp Asp Ala Tyr Cys Tyr Asn Pro His
                85                  90                  95

Ala

<210> SEQ ID NO 3
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Gly Val Tyr His Arg Glu Ala Ala Ser Gly Lys Tyr Lys Leu Thr Tyr
1               5                   10                  15

Ala Glu Ala Lys Ala Val Cys Glu Phe Glu Gly Gly His Leu Ala Thr
                20                  25                  30

Tyr Lys Gln Leu Glu Ala Ala Arg Lys Ile Gly Phe His Val Cys Ala
            35                  40                  45

Ala Gly Trp Met Ala Lys Gly Arg Val Gly Tyr Pro Ile Val Lys Pro
50                  55                  60

Gly Pro Asn Cys Gly Phe Gly Lys Thr Gly Ile Ile Asp Tyr Gly Ile
65                  70                  75                  80

Arg Leu Asn Arg Ser Glu Arg Trp Asp Ala Tyr Cys Tyr Asn Pro His
                85                  90                  95

Ala

<210> SEQ ID NO 4
<211> LENGTH: 99
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Ala Cys Gly Val Tyr His Arg Glu Ala Gln Ser Gly Lys Tyr Lys Leu
1               5                   10                  15

Thr Tyr Ala Glu Ala Lys Ala Val Cys Glu Phe Glu Gly Gly His Leu
                20                  25                  30

Ala Thr Tyr Lys Gln Leu Glu Cys Ala Arg Lys Ile Gly Phe His Val
            35                  40                  45

Cys Ala Ala Gly Trp Met Ala Lys Gly Arg Val Gly Tyr Pro Ile Val
50                  55                  60

Lys Pro Gly Pro Asn Cys Gly Phe Gly Lys Thr Gly Ile Ile Asp Tyr
65                  70                  75                  80

Gly Ile Arg Leu Asn Arg Ser Glu Arg Trp Asp Ala Tyr Cys Tyr Asn
                85                  90                  95

Pro His Ala

<210> SEQ ID NO 5
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 5

Gly Val Tyr His Arg Glu Ala Gln Ser Gly Lys Tyr Lys Leu Thr Tyr
1               5                   10                  15

Ala Glu Ala Lys Ala Val Cys Glu Phe Glu Gly Gly His Leu Cys Thr
            20                  25                  30

Tyr Lys Gln Leu Glu Ala Ala Arg Lys Ile Gly Phe His Val Cys Ala
        35                  40                  45

Ala Gly Trp Met Ala Lys Gly Arg Val Gly Tyr Pro Ile Val Lys Pro
    50                  55                  60

Gly Pro Asn Cys Gly Phe Gly Lys Thr Gly Ile Ile Asp Tyr Gly Ile
65                  70                  75                  80

Arg Leu Asn Arg Ser Glu Arg Trp Asp Ala Tyr Cys Cys Asn Pro His
                85                  90                  95

Ala

<210> SEQ ID NO 6
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 6

Gly Gly Gly Gly Gly Ser Gly Gly Gly Val Tyr His Arg Glu
1               5                   10                  15

Ala Gln Ser Gly Lys Tyr Tyr Leu Thr Tyr Ala Glu Ala Lys Ala Val
            20                  25                  30

Cys Glu Phe Glu Gly Gly His Leu Ala Thr Tyr Lys Gln Leu Glu Ala
        35                  40                  45

Ala Arg Lys Ile Gly Phe His Val Cys Ala Ala Gly Trp Met Ala Lys
    50                  55                  60

Gly Arg Val Gly Tyr Pro Ile Val Lys Pro Gly Pro Asn Cys Gly Phe
65                  70                  75                  80

Gly Lys Thr Gly Ile Ile Asp Tyr Gly Ile Arg Leu Asn Arg Ser Glu
                85                  90                  95

Arg Trp Asp Ala Tyr Cys Tyr Asn Pro His Ala Gly Gly Ser His His
            100                 105                 110

His His His His
        115

<210> SEQ ID NO 7
<211> LENGTH: 99
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 7

Ala Cys Gly Val Tyr His Arg Glu Ala Gln Ser Gly Lys Tyr Lys Leu
1               5                   10                  15

Thr Tyr Ala Glu Ala Lys Ala Val Cys Glu Phe Glu Gly Gly His Leu
            20                  25                  30

```
Ala Thr Tyr Lys Gln Leu Glu Cys Ala Arg Lys Ile Gly Phe His Val
         35                  40                  45

Cys Ala Ala Gly Trp Met Ala Lys Gly Arg Val Gly Tyr Pro Ile Val
 50                  55                  60

Lys Pro Gly Pro Asn Cys Gly Phe Gly Lys Thr Gly Ile Ile Asp Tyr
 65                  70                  75                  80

Gly Ile Arg Leu Asn Arg Ser Glu Arg Trp Asp Ala Tyr Cys Tyr Asn
                 85                  90                  95

Pro His Ala

<210> SEQ ID NO 8
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Gly Val Tyr His Arg Glu Ala Ile Ser Gly Lys Tyr Tyr Leu Thr Tyr
 1               5                  10                  15

Ala Glu Ala Lys Ala Val Cys Glu Phe Glu Gly Gly His Leu Ala Thr
                 20                  25                  30

Tyr Lys Gln Leu Leu Ala Ala Gln Lys Ile Gly Phe His Val Cys Ala
         35                  40                  45

Ala Gly Trp Met Ala Lys Gly Arg Val Gly Tyr Pro Ile Val Lys Pro
 50                  55                  60

Gly Pro Asn Cys Gly Phe Gly Lys Thr Gly Ile Ile Asp Tyr Gly Ile
 65                  70                  75                  80

Arg Leu Asn Arg Ser Glu Arg Trp Asp Ala Tyr Cys Tyr Asn Pro His
                 85                  90                  95

Ala

<210> SEQ ID NO 9
<211> LENGTH: 97
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Gly Val Tyr His Arg Glu Ala Ile Ser Gly Lys Tyr Tyr Leu Thr Tyr
 1               5                  10                  15

Ala Glu Ala Lys Ala Val Cys Glu Phe Glu Gly Gly His Leu Ala Thr
                 20                  25                  30

Tyr Lys Gln Leu Gln Ala Ala Gln Lys Ile Gly Phe His Val Cys Ala
         35                  40                  45

Ala Gly Trp Met Ala Lys Gly Arg Val Gly Tyr Pro Ile Val Lys Pro
 50                  55                  60

Gly Pro Asn Cys Gly Phe Gly Lys Thr Gly Ile Ile Asp Tyr Gly Ile
 65                  70                  75                  80

Arg Leu Asn Arg Ser Glu Arg Trp Asp Ala Tyr Cys Tyr Asn Pro His
                 85                  90                  95

Ala
```

-continued

```
<210> SEQ ID NO 10
<211> LENGTH: 99
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Ala Cys Gly Val Tyr His Arg Glu Ala Ile Ser Gly Lys Tyr Tyr Leu
1               5                   10                  15

Thr Tyr Ala Glu Ala Lys Ala Val Cys Glu Phe Glu Gly Gly His Leu
            20                  25                  30

Ala Thr Tyr Lys Gln Leu Leu Ala Ala Gln Lys Ile Gly Phe His Val
        35                  40                  45

Cys Ala Ala Gly Trp Met Ala Lys Gly Arg Val Gly Tyr Pro Ile Val
    50                  55                  60

Lys Pro Gly Pro Asn Cys Gly Phe Gly Lys Thr Gly Ile Ile Asp Tyr
65                  70                  75                  80

Gly Ile Arg Leu Asn Arg Ser Glu Arg Trp Asp Ala Tyr Cys Tyr Asn
                85                  90                  95

Pro His Ala

<210> SEQ ID NO 11
<211> LENGTH: 99
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Ala Cys Gly Val Tyr His Arg Glu Ala Ile Ser Gly Lys Tyr Tyr Leu
1               5                   10                  15

Thr Tyr Ala Glu Ala Lys Ala Val Cys Glu Phe Glu Gly Gly His Leu
            20                  25                  30

Ala Thr Tyr Lys Gln Leu Gln Ala Ala Gln Lys Ile Gly Phe His Val
        35                  40                  45

Cys Ala Ala Gly Trp Met Ala Lys Gly Arg Val Gly Tyr Pro Ile Val
    50                  55                  60

Lys Pro Gly Pro Asn Cys Gly Phe Gly Lys Thr Gly Ile Ile Asp Tyr
65                  70                  75                  80

Gly Ile Arg Leu Asn Arg Ser Glu Arg Trp Asp Ala Tyr Cys Tyr Asn
                85                  90                  95

Pro His Ala

<210> SEQ ID NO 12
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Gly Gly Gly Gly Gly Ser Gly Gly Gly Ala Cys Gly Val Tyr His
1               5                   10                  15

Arg Glu Ala Gln Ser Gly Lys Tyr Tyr Leu Thr Tyr Ala Glu Ala Lys
```

```
                     20                  25                  30
Ala Val Cys Glu Phe Glu Gly Gly His Leu Ala Thr Tyr Lys Gln Leu
            35                  40                  45

Glu Cys Ala Arg Lys Ile Gly Phe His Val Cys Ala Ala Gly Trp Met
        50                  55                  60

Ala Lys Gly Arg Val Gly Tyr Pro Ile Val Lys Pro Gly Pro Asn Cys
65                  70                  75                  80

Gly Phe Gly Lys Thr Gly Ile Ile Asp Tyr Gly Ile Arg Leu Asn Arg
                85                  90                  95

Ser Glu Arg Trp Asp Ala Tyr Cys Tyr Asn Pro His Ala Gly Gly Ser
            100                 105                 110

Glu Phe Arg His Asp Ser
            115

<210> SEQ ID NO 13
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Gly Gly Gly Gly Gly Ser Gly Gly Gly Ala Cys Gly Val Tyr His
1               5                   10                  15

Arg Glu Ala Gln Ser Gly Lys Tyr Tyr Leu Thr Tyr Ala Glu Ala Lys
            20                  25                  30

Ala Val Cys Glu Phe Glu Gly Gly His Leu Ala Thr Tyr Lys Gln Leu
            35                  40                  45

Glu Cys Ala Arg Lys Ile Gly Phe His Val Cys Ala Ala Gly Trp Met
        50                  55                  60

Ala Lys Gly Arg Val Gly Tyr Pro Ile Val Lys Pro Gly Pro Asn Cys
65                  70                  75                  80

Gly Phe Gly Lys Thr Gly Ile Ile Asp Tyr Gly Ile Arg Leu Asn Arg
                85                  90                  95

Ser Glu Arg Trp Asp Ala Tyr Cys Tyr Asn Pro His Ala Gly Gly Ser
            100                 105                 110

His His His His His His
            115

<210> SEQ ID NO 14
<211> LENGTH: 294
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 14
ggagtctatc acagagaggc tagatcaggc aagtataagc tgacctacgc cgaggctaag     60
gccgtgtgcg agttcgaggg cggtcacctg gctacctata agcagctgga agccgctaga   120
aagatcggct ttcacgtgtg cgccgctggc tggatggcta agggtagagt gggctaccct   180
atcgtgaagc ctggccctaa ctgcggcttc ggtaaaaccg gaattatcga ctacgggatt   240
aggctgaata gatcagagcg ctgggacgcc tactgctata accctcacgc taag          294
```

```
<210> SEQ ID NO 15
<211> LENGTH: 291
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 15
ggagtctatc acagagaggc tcagtcaggc aagtataagc tgacctacgc cgaggctaag      60
gccgtgtgcg agttcgaggg cggtcacctg gctacctata agcagctgga agccgctaga     120
aagatcggct ttcacgtgtg cgccgctggc tggatggcta agggtagagt gggctaccct     180
atcgtgaagc ctggccctaa ctgcggcttc ggtaaaaccg gaattatcga ctacgggatt     240
aggctgaata gatcagagcg ctgggacgcc tactgctata accctcacgc c              291

<210> SEQ ID NO 16
<211> LENGTH: 291
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 16
ggagtctatc acagagaggc tgctagcggt aaatacaagc tgacctacgc cgaggctaag      60
gccgtgtgcg agttcgaggg cggtcacctg gctacctata agcagctgga agccgctaga     120
aagatcggct ttcacgtgtg cgccgctggc tggatggcta agggtagagt gggctaccct     180
atcgtgaagc ctggccctaa ctgcggcttc ggtaaaaccg gaattatcga ctacgggatt     240
aggctgaata gatcagagcg ctgggacgcc tactgctata accctcacgc c              291

<210> SEQ ID NO 17
<211> LENGTH: 300
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 17
ggcgcctgtg gcgtgtatca cagggaggcc cagagcggca agtacaagct cacctacgcc      60
gaggccaagg ccgtgtgcga attcgagggc ggccacctgg ccacctacaa gcagctggag     120
tgcgccagga agatcggctt ccacgtgtgt gccgccggct ggatggccaa aggcagagtg     180
ggctacccca tcgtgaaacc cggccccaac tgcggcttcg gcaagacagg catcatcgac     240
tacggcatca ggctgaacag gagcgagagg tgggacgcct actgctacaa ccccacgcc     300

<210> SEQ ID NO 18
<211> LENGTH: 291
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 18
ggagtgtatc acagagaggc ccagagcggc aagtacaagc tgacctacgc cgaggccaag      60
```

```
gccgtgtgtg agttcgaggg cggccacctg tgcacctaca agcagctgga ggccgccagg    120
aagatcggct tccacgtgtg tgccgccggc tggatggcta aaggcagggt gggctacccc    180
attgtgaagc ccggccccaa ttgcggcttc ggcaagaccg gcatcatcga ctacggcatc    240
aggctgaaca ggagcgagag gtgggacgcc tactgctgca accccacgc c              291

<210> SEQ ID NO 19
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 19

His His His His His His
1               5

<210> SEQ ID NO 20
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Leu Pro Glu Thr Gly Gly Gly
1               5
```